US012358370B2

(12) United States Patent
Shishavan et al.

(10) Patent No.: US 12,358,370 B2
(45) Date of Patent: Jul. 15, 2025

(54) CLOSED-LOOP REAL TIME SSVEP-BASED HEADS-UP DISPLAY TO CONTROL IN VEHICLE FEATURES USING DEEP LEARNING

(71) Applicants: Toyota Motor Engineering & Manufacturing North America, Inc., Plano, TX (US); University of Connecticut Health Center, Farmington, CT (US)

(72) Inventors: Hossein Hamidi Shishavan, New Britain, CT (US); Insoo Kim, Avon, CT (US); Mohammad Behzadi, Storrs, CT (US); Ercan Dede, Ann Arbor, MI (US); Danny Lohan, Ann Arbor, MI (US)

(73) Assignees: Toyota Motor Engineering & Manufacturing North America, Inc., Plano, TX (US); University of Connecticut Health Center, Farmington, CT (US)

( * ) Notice: Subject to any disclaimer, the term of this patent is extended or adjusted under 35 U.S.C. 154(b) by 292 days.

(21) Appl. No.: 18/067,473

(22) Filed: Dec. 16, 2022

(65) Prior Publication Data

US 2024/0198798 A1 Jun. 20, 2024

(51) Int. Cl.
*B60K 35/00* (2024.01)
*A61B 5/00* (2006.01)
*A61B 5/372* (2021.01)
*B60K 35/10* (2024.01)
*B60K 35/23* (2024.01)

(Continued)

(52) U.S. Cl.
CPC .............. *B60K 35/00* (2013.01); *A61B 5/372* (2021.01); *A61B 5/725* (2013.01); *A61B 5/7257* (2013.01); *A61B 5/7267* (2013.01); *G06N 3/0464* (2023.01); *B60K 35/10* (2024.01); *B60K 35/23* (2024.01); *B60K 35/29* (2024.01);

(Continued)

(58) Field of Classification Search
None
See application file for complete search history.

(56) References Cited

U.S. PATENT DOCUMENTS 9,354,702 B2    5/2016  Mullins
10,335,572 B1*  7/2019  Kumar .................... G06F 3/015

(Continued)

FOREIGN PATENT DOCUMENTS

CN    211001203 U    7/2020
CN    112000087 A    11/2020
CN    113435234 A    9/2021

*Primary Examiner* — Daniel L Greene
*Assistant Examiner* — Robert L Pinkerton
(74) *Attorney, Agent, or Firm* — DINSMORE & SHOHL LLP (57) ABSTRACT

A vehicle system includes a controller programmed to display a plurality of icons on a heads-up-display (HUD) of the vehicle, receive electroencephalography (EEG) data from a driver of the vehicle, perform a Fast Fourier Transform of the EEG data to obtain an EEG spectrum, input the EEG spectrum into a trained machine learning model, determine which of the plurality of icons the driver is viewing based on an output of the trained machine learning model, and perform one or more vehicle operations based on the output of the trained machine learning model.

20 Claims, 8 Drawing Sheets

(51) Int. Cl.
  *B60K 35/29* (2024.01)
  *G06N 3/0464* (2023.01)
(52) U.S. Cl.
  CPC ... *B60K 2360/119* (2024.01); *B60K 2360/149* (2024.01); *B60K 2360/188* (2024.01)

(56) References Cited

U.S. PATENT DOCUMENTS

| | | | |
|---|---|---|---|
| 10,706,631 | B2 | 7/2020 | Schmit et al. |
| 10,864,918 | B2 | 12/2020 | An |
| 2019/0200977 | A1* | 7/2019 | Shelton, IV ............ A61B 34/20 |
| 2020/0074197 | A1* | 3/2020 | Upmanue ............. B60K 35/60 |
| 2020/0217950 | A1* | 7/2020 | Unnikrishnan ....... G01S 13/931 |
| 2021/0267474 | A1* | 9/2021 | Wang ..................... A61B 5/117 |
| 2021/0286429 | A1* | 9/2021 | Azemi ................... G06N 3/045 |
| 2022/0259678 | A1* | 8/2022 | Phillips .................. C12Q 1/686 |
| 2023/0058082 | A1* | 2/2023 | Kim ................... G06V 10/7788 |
| 2023/0157621 | A1* | 5/2023 | De Venuto ........... A61B 5/4842 |
| | | | 600/301 |
| 2023/0162001 | A1* | 5/2023 | Nishimura ............. G06N 3/082 |
| | | | 706/26 |
| 2023/0351633 | A1* | 11/2023 | Chen ..................... B60K 35/80 |
| 2024/0303927 | A1* | 9/2024 | Birenbaum ........... G06V 10/26 |

* cited by examiner

CLOSED-LOOP REAL TIME SSVEP-BASED HEADS-UP DISPLAY TO CONTROL IN VEHICLE FEATURES USING DEEP LEARNING

TECHNICAL FIELD

The present specification relates to vehicle systems, and more particularly, to a closed-loop real time SSVEP-based heads-up display to control in vehicle features using deep learning.

BACKGROUND

Many vehicle crashes that occur result from distracted driving. In many instances, a driver becomes distracted due to involvement in or operation of in-vehicle features (e.g., using components or controls integral to the vehicle). Accordingly, technology that facilitates the use of in-vehicle features by a driver without distracting the driver may be desirable.

SUMMARY

In one embodiment, a vehicle system may include a controller. The controller may be programmed to display a plurality of icons on a HUD of a vehicle, receive EEG data from a driver of the vehicle, perform an FFT of the EEG data to obtain an EEG spectrum, input the EEG spectrum into a trained machine learning model, determine which of the plurality of icons the driver is viewing based on an output of the trained machine learning model, and perform one or more vehicle operations based on the output of the trained machine learning model in real time.

In another embodiment, a method may include displaying a plurality of icons on a HUD of a vehicle, receiving EEG data from a driver of the vehicle, performing an FFT of the EEG data to obtain an EEG spectrum, inputting the EEG spectrum into a trained machine learning model, determining which of the plurality of icons the driver is viewing based on an output of the trained machine learning model, and performing one or more vehicle operations based on the input of the trained machine learning model.

In another embodiment, a method may include receiving training data comprising EEG data collected from a plurality of individual subjects while each subject is viewing specific icons, performing an FFT of the training data to obtain EEG spectrum data, and training a machine learning model to predict which icon the subjects are viewing based on the EEG spectrum data.

BRIEF DESCRIPTION OF THE DRAWINGS

The embodiments set forth in the drawings are illustrative and exemplary in nature and not intended to limit the disclosure. The following detailed description of the illustrative embodiments can be understood when read in conjunction with the following drawings, where like structure is indicated with like reference numerals and in which.

DETAILED DESCRIPTION

The embodiments disclosed herein provide a system and method for deep learning for steady state visually evoked potentials (SSVEP) detection in a vehicle. Steady state visually evoked potentials are signals that are natural responses of human beings to visual stimulation at specific frequencies. When an individual's retina is excited by a visual stimulus ranging from about 3.5 Hz to 75 Hz, the individual's brain generates electrical activity at the same frequency or at multiples of the frequency of the visual stimulus. As such, this can be utilized as a method for monitoring brain activity.

In one embodiment, a vehicle system of a vehicle may include a controller. The controller may be programmed to display a plurality of icons on a heads-up-display (HUD) of a vehicle, receive electroencephalography (EEG) data from a driver of the vehicle, perform an FFT of the EEG data to obtain an EEG spectrum, input the EEG spectrum into a trained machine learning model, determine which of the plurality of icons the driver is looking at based on an output of the trained machine learning model, and perform one or more vehicle operations based on the output of the trained machine learning model.

Figure 1:
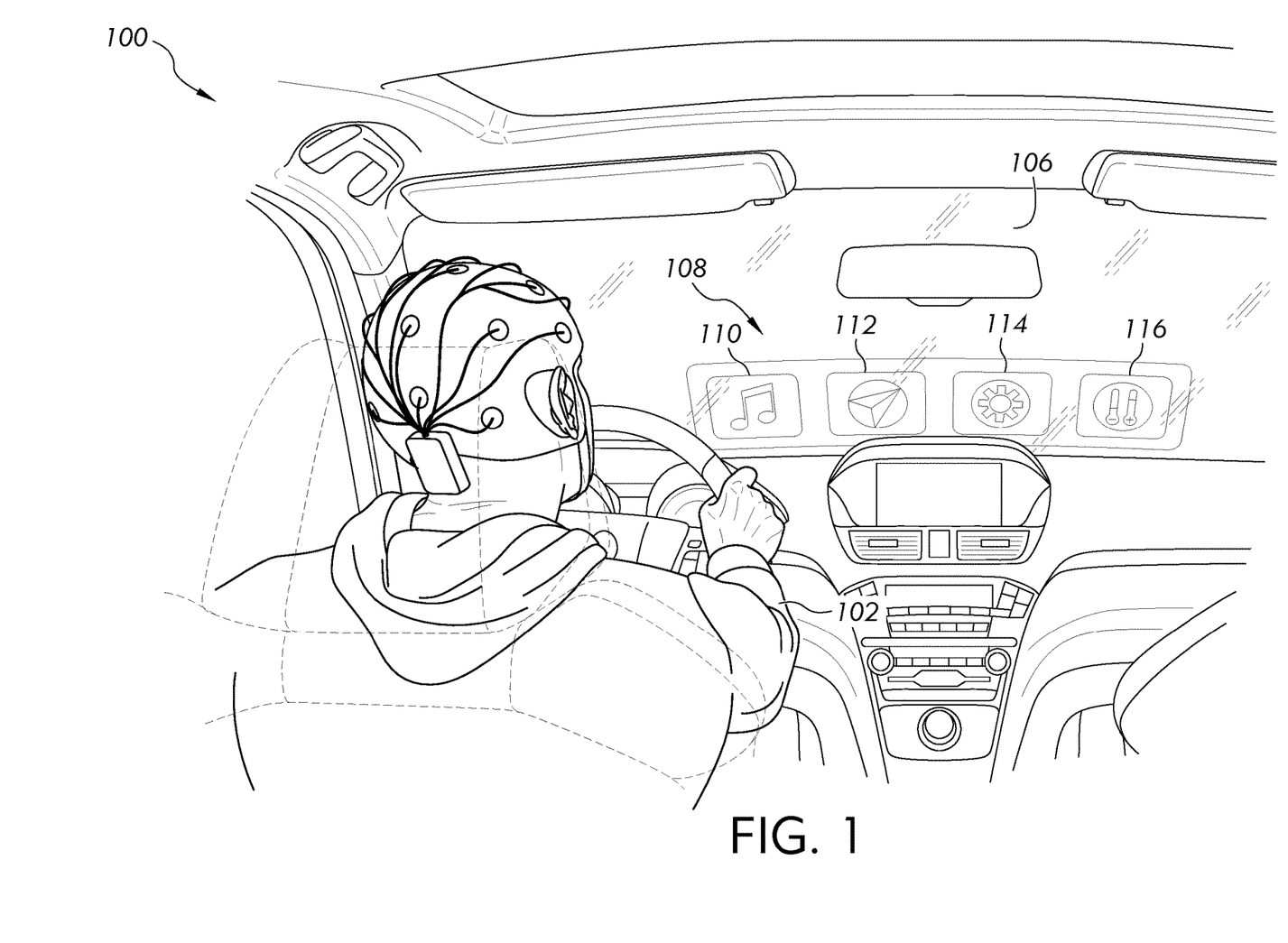
FIG. 1 depicts an example vehicle interior, according to one or more embodiments shown and described herein.

Turning now to the figures, FIG. 1 depicts an interior of a vehicle 100. A driver 102 is seated in a driver's seat of the vehicle 100 and drives the vehicle 100. A head-mounted device 104 that reads brain waves of the driver 102 may be worn by the driver 102, as disclosed herein. The windshield 106 or other surface of the vehicle 100 displays a HUD 108. In embodiments, the HUD 108 is a transparent display that can display text, images, or other information that can be seen by the driver 102 without looking away from the windshield 106 or other surface and thereby avoiding taking their eyes off the road.

In the example of FIG. 1, the HUD 108 displays icons 110, 112, 114, and 116. While four icons are displayed on the HUD 108 in the example of FIG. 1, it should be understood that in other examples, any number of icons may be displayed by the HUD 108 in any orientation. The icons 110, 112, 114, 116 each have a different shape and/or a different color. As such, when the driver 102 views one of the icons 110, 112, 114, 116, a particular SSVEP response will be triggered in the driver's brain depending on which icon the driver 102 is viewing. In the illustrated example, icons that are green or black and white showed the best performances. However, any colors may be used for the icons. The particular SSVEP response that is generated can be detected by the head-mounted device 104, as disclosed herein, thereby indicating which icon the driver 102 is viewing.

By detecting which icon displayed by the HUD 108 that the driver 102 is viewing, the driver 102 may control certain functions of the vehicle 100 without taking their eyes off the road and without the need to use their hands to manually press any buttons or switches. In particular, when the driver 102 views a particular icon, a vehicle system of the vehicle 100 may recognize which icon is being looked at and may either cause the HUD 108 to display additional icons (e.g., a sub-menu) or cause a particular vehicle function to operate. For example, the icon 110 may lead to a sub-menu related to audio options, the icon 112 may lead to a sub-menu of navigation options, the icon 114 may lead to a sub-menu of settings, and the icon 116 may lead to a sub-menu of temperature options. A sub-menu may display additional icons on the HUD 108 that the driver 102 can activate by viewing. For example, when the driver 102 views the icon 116, a sub-menu may display additional icons that may let the driver 102 set a vehicle temperature for a heating or cooling system of the vehicle 100.

As discussed above, the head-mounted device 104 may detect brain waves generated by the driver 102. In embodiments, the head-mounted device 104 may include a plurality of electrodes that detect electrical signals generated by the brain of the driver 102. In embodiments, the head-mounted device 104 uses electroencephalography (EEG) to measure electrical activity in the driver's brain. However, in other examples, the head-mounted device 104 may detect brain waves of the driver 102 in other manners. The brain waves detected by the head-mounted device 104 may transmit detected brain waves to a vehicle system of the vehicle 100, as discussed in further detail below. In one example, the head-mounted device 104 is a g. Nautilus™ headset device. However, in other examples, the head-mounted device 104 may include other devices that perform the functions disclosed herein.

Figure 2:
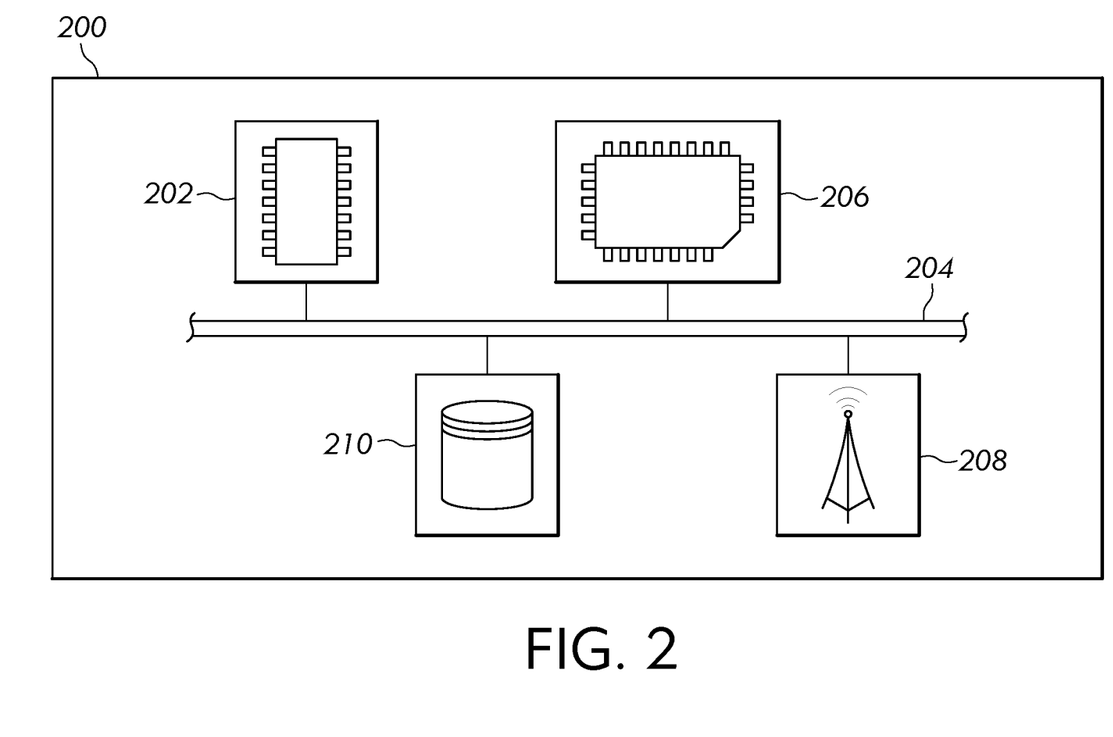
FIG. 2 depicts a schematic diagram of a vehicle system, according to one or more embodiments shown and described herein.

FIG. 2 depicts a vehicle system 200 that may be included in the vehicle 100 of FIG. 1. In the example of FIG. 2, the vehicle system 200 includes one or more processors 202, a communication path 204, one or more memory modules 206, a network interface hardware 208, and a data storage component 210, the details of which will be set forth in the following paragraphs.

Each of the one or more processors 202 may be any device capable of executing machine readable and executable instructions. Accordingly, each of the one or more processors 202 may be a controller, an integrated circuit, a microchip, a computer, or any other computing device. In some examples, one or more of the processors 202 may comprise a graphics processing unit (GPU).

The one or more processors 202 are coupled to a communication path 204 that provides signal interconnectivity between various modules of the vehicle system 200. Accordingly, the communication path 204 may communicatively couple any number of processors 202 with one another, and allow the modules coupled to the communication path 204 to operate in a distributed computing environment. Specifically, each of the modules may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

Accordingly, the communication path 204 may be formed from any medium that is capable of transmitting a signal such as, for example, conductive wires, conductive traces, optical waveguides, or the like. In some embodiments, the communication path 204 may facilitate the transmission of wireless signals, such as Wi-Fi, Bluetooth®, Near Field Communication (NFC) and the like. Moreover, the communication path 204 may be formed from a combination of mediums capable of transmitting signals. In one embodiment, the communication path 204 comprises a combination of conductive traces, conductive wires, connectors, and buses that cooperate to permit the transmission of electrical data signals to components such as processors, memories, sensors, input devices, output devices, and communication devices. Accordingly, the communication path 204 may comprise a vehicle bus, such as for example a LIN bus, a CAN bus, a VAN bus, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The vehicle system 200 includes one or more memory modules 206 coupled to the communication path 204. The one or more memory modules 206 may include RAM, ROM, flash memories, hard drives, or any device capable of storing machine readable and executable instructions such that the machine readable and executable instructions can be accessed by the one or more processors 202. The machine readable and executable instructions may comprise logic or algorithm(s) written in any programming language of any generation (e.g., 1GL, 2GL, 3GL, 4GL, or 5GL) such as, for example, machine language that may be directly executed by the processor, or assembly language, object-oriented programming (OOP), scripting languages, microcode, etc., that may be compiled or assembled into machine readable and executable instructions and stored on the one or more memory modules 206. Alternatively, the machine readable and executable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components.

Still referring to FIG. 2, the vehicle system 200 includes network interface hardware 208 for communicatively coupling the vehicle system 200 to the head-mounted device 104. In some examples, the network interface hardware 208 may also couple the vehicle system 200 to one or more other external devices including, such as a remote computing device (e.g., a cloud server or edge server) or other vehicles. The network interface hardware 208 can be communicatively coupled to the communication path 204 and can be any device capable of transmitting and/or receiving data via a network or via a hard-wired connection (e.g., a cable connection) with the head-mounted device 104. In some examples, the network interface hardware 208 can include a communication transceiver for sending and/or receiving any wired or wireless communication. For example, the network interface hardware 208 may include an antenna, a modem, LAN port, Wi-Fi card, WiMax card, mobile communications hardware, near-field communication hardware, satellite communication hardware and/or any wired or wireless hardware for communicating with the head-mounted device 104 and/or other networks and/or devices. In one embodiment, the network interface hardware 208 includes hardware configured to operate in accordance with the Bluetooth® wireless communication protocol. In the illustrated example, the network interface hardware 208 of the vehicle system 200 may receive brain wave data collected by the head-mounted device 104, as disclosed in further detail below.

Still referring to FIG. 2, the vehicle system 200 includes a data storage component 210. The data storage component 210 may store data used by various components of the vehicle system 200. In particular, the data storage component 210 may store brain wave data received from the head-mounted device 104. The data storage component 210 may also store parameters of a model maintained by the vehicle system 200 to analyze the brain wave data from the head-mounted device 104, as disclosed herein.

Figure 3:
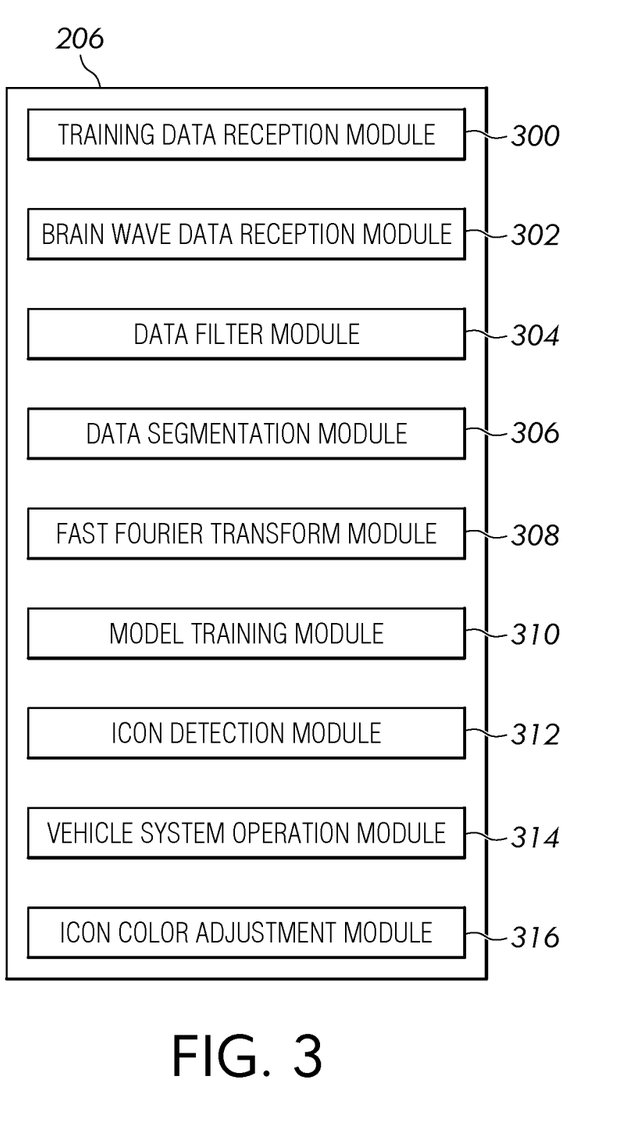
FIG. 3 depicts a schematic diagram of one or more memory modules of the vehicle system of FIG. 2, according to one or more embodiments shown and described herein.

Now referring to FIG. 3, the one or more memory modules 206 of the vehicle system 200 include a training data reception module 300, a brain wave data reception module 302, a data filter module 304, a data segmentation module 306, a Fast Fourier Transform (FFT) module 308, a model training module 310, an icon detection module 312, a vehicle system operation module 314, and an icon color adjustment module 316. Each of the training data reception module 300, the brain wave data reception module 302, the data filter module 304, the data segmentation module 306, the FFT module 308, the model training module 310, the icon detection module 312, the vehicle system operation module 314, and the icon color adjustment module 316 may be a program module in the form of operating systems, application program modules, and other program modules stored in the one or more memory modules 206. Such a program module may include, but is not limited to, routines, subroutines, programs, objects, components, data structures and the like for performing specific tasks or executing specific data types as will be described below.

In some examples, the program module may be stored in a remote storage device that may communicate with the vehicle system 200. In some examples, the functions of one or more of the memory modules 206 may be performed by a remote computing device (e.g., an edge server or a cloud computing device) that is communicatively coupled to the vehicle system 200. For example, the vehicle system 200 may transmit data received from the head-mounted device 104 to a cloud server for processing.

The training data reception module 300 may include programming instructions to receive training data that may be used to train the model maintained by the vehicle system 200, as disclosed herein. After the model is trained, the model may be operated in real-time to determine which icons displayed on the HUD 108 the driver 102 is viewing, as disclosed herein. In addition, after the model is trained, the model may be periodically updated and re-trained with additional training data. In some examples, the training data reception module 300 may include programming instructions to receive training data from the head-mounted device 104. In other examples, the training data reception module 300 may include programming instructions to receive training data from another source (e.g., a computing device that collects the training data).

In embodiments, the training data received by the training data reception module 300 includes EEG data collected from a plurality of individual subjects while each subject is viewing specific icons while wearing the head-mounted device 104 during a training session. In some examples, training sessions are conducted while a subject is in the vehicle 100. In other examples, training sessions may be conducted while a subject is in a simulation environment that simulates the interior of the vehicle 100.

While collecting data during a training session, a conductive paste may be applied between the electrodes of the head-mounted device 104 and the subject's skin to bring impedances below 5 kΩ to reduce vulnerability to electrical artifacts and/or movement. Channels from the parietal region and the visual cortex at the occipital region are ideal selections for recording SSVEP, although signals from the parietal lobe has lower SSVEP potential.

In embodiments, based on the international 10-20 system for describing locations of scalp electrodes, sixteen electrodes of the head-mounted device 104 were placed at Fz, Cz, CPz, P1, Pz, P2, PO3, POz, PO4, PO7, PO8, O1, Oz, O2, TP9, and TP10. A reference electrode is connected to the mastoid, and a ground electrode is connected to AFz. However, in other examples, the electrodes of the head-mounted device 104 may be placed at other locations. In the illustrated example, data is collected by the head-mounted device 104 with a 500 Hz resolution. However, in other examples, the head-mounted device 104 may collect data with any other resolution.

In embodiments, the training data collected from each subject includes a calibration data set. That is, particular sets of icons are presented to the subject via the HUD 108 at predetermined intervals during a training session, and the individual is instructed to look at a particular icon in the set in a predetermined pattern during the training session. As such, it is known what icon the individual is viewing during each point in time during the training session. Accordingly, EEG data can be collected from the head-mounted device 104 during the training session, and the icons that the subject is viewing during the training session can be used as ground truth values to train the model.

In the illustrated example, each set of icons is displayed on the HUD 108 for 3 seconds during a training session, and the subject is instructed to look at a particular icon during those 3 seconds. A plurality of different sets of icons may be displayed to the subject in a predetermined or random pattern. Each icon is intended to trigger a different SSVEP response by the subject. Accordingly, in the illustrated example, training data is collected in 3 second intervals while a particular set of icons is being displayed to the subject. However, in other examples, the sets of icons may be displayed for a longer or shorter time than 3 seconds, and data may be collected for a corresponding time interval. After the training data reception module 300 receives the training data, the training data may be used to train the model maintained by the vehicle system 200, as discussed in further detail below.

Referring still to FIG. 3, the brain wave data reception module 302 may include programming instructions to receive brain wave data from the head-mounted device 104 during real-time operation, as disclosed herein. In particular, once the model is trained, brain wave data from the head-mounted device 104 may be received while the driver 102 is viewing a particular icon on the HUD 108. The brain wave data received by the brain wave data reception module 302 may be input into the trained model to determine which icon the driver 102 is viewing, as disclosed herein. Certain vehicle functionality of the vehicle 100 may then be operated depending on which icon the driver 102 is viewing, as disclosed herein.

Referring still to FIG. 3, the data filter module 304, the data segmentation module 306, and the FFT module 308 may include programming instructions to perform data preprocessing before data is input to the model, as disclosed herein. In particular, the data filter module 304 may include programming instructions to filter brain wave data received by the training data reception module 300 or the brain wave data reception module 302. The data filter module 304 may include programming instructions to apply a filter to received brain wave data to remove environmental noises and keep dated related to the SSVEP frequencies. In the illustrated example, the data filter module 304 applies a 4$^{th}$ order Butterworth band pass filter between 3-40 Hz. However, in other examples, other types of filters may be used.

Referring still to FIG. 3, the data segmentation module 306 may include programming instructions to segment brain wave data received by the training data reception module 300 or the brain wave data reception module 302. In the illustrated example, the data segmentation module 306 includes programming instructions to segment received brain wave data into segments of 0.25 seconds. However, in other examples, other data segment lengths may be used.

Referring still to FIG. 3, the FFT module 308 may perform a Fast Fourier Transform (FFT) on the data filtered by the data filter module 304 and segmented by the data segmentation module 306. In particular, the FFT module 308 includes programming instructions to obtain a complex spectrum for each data segment generated by the data segmentation module 306. The complex spectrum obtained by the FFT module 308 may be represented as:

$$X_{comp} = \text{Concatenate}(\text{Re}\{FFT(\text{input})\}, \text{Im}\{FFT(\text{input})\});$$

where Re{FFT(input)} is the real part and Im{FFT(input)} is the imaginary part of the time segment inputs. That is, the magnitude and phase information is combined and provided as input to the model, as disclosed herein.

In the illustrated example, the FFT module 308 uses a start frequency of 3 Hz and an end frequency of 35 Hz. However, in other examples, other start and end frequencies may be used. The length of the FFT vector can be obtained using the following equation:

$$\text{Output size of } FFT = 2 \times \left( \frac{\text{End frequency}}{\text{Resolution}} + 1 - \frac{\text{Start frequency}}{\text{Resolution}} \right)$$

Referring still to FIG. 3, the model training module 310 may include programming instructions to train the model maintained by the vehicle system 200, as disclosed herein. In particular, the model training module 310 may include programming instructions to receive training data that has been preprocessed by the data filter module 304, the data segmentation module 306, and the FFT module 308, as described above, and train the model to predict which icon on the HUD 108 the driver 102 is viewing based on brain wave data.

Figure 4:
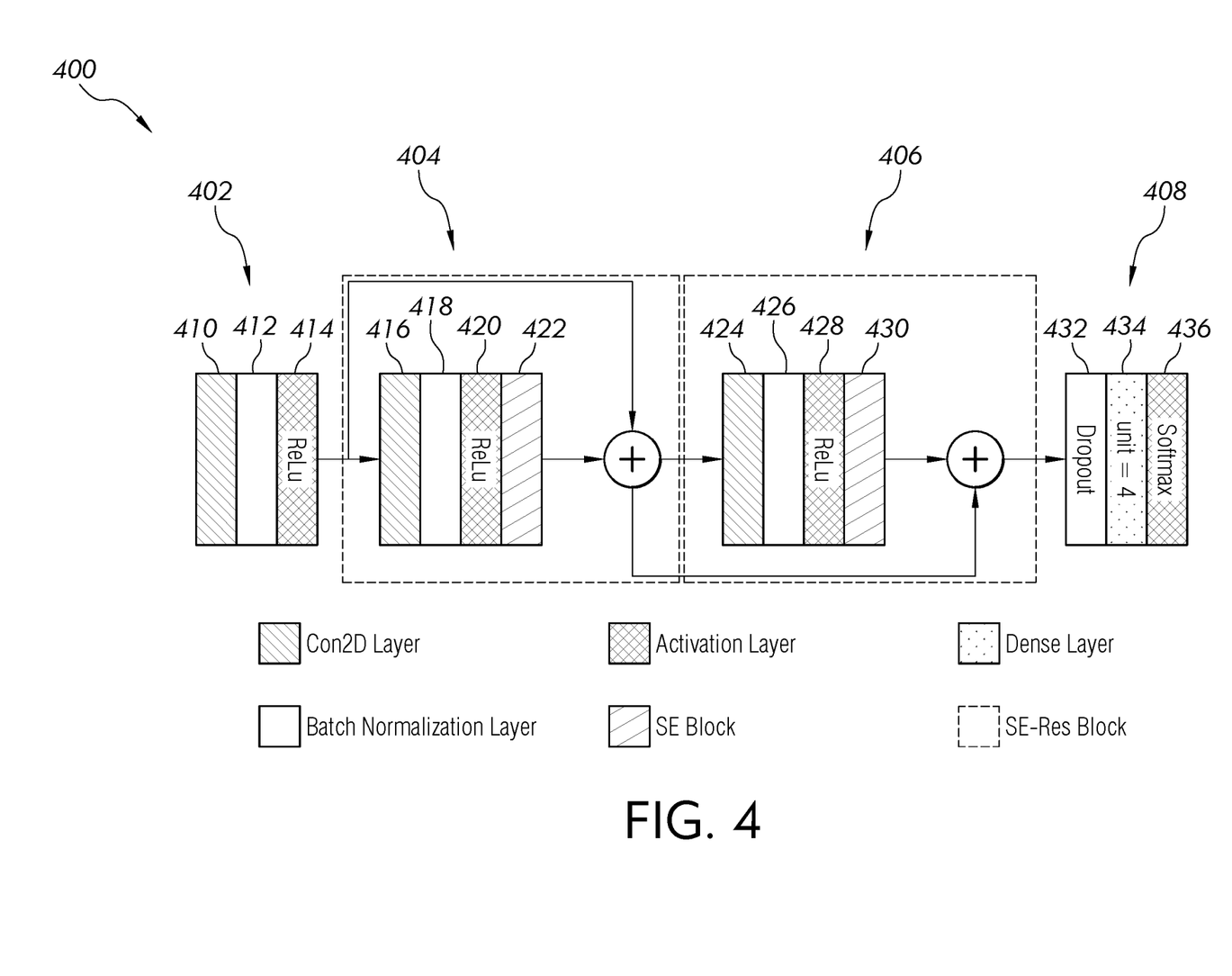
FIG. 4 depicts a schematic diagram of an example machine learning model maintained by the vehicle system of FIG. 2, according to one or more embodiments shown and described herein.

An example architecture of a model 400 maintained by the vehicle system 200 is shown in FIG. 4. In the example of FIG. 4, the model 400 includes a convolutional neural network (CNN). The model 400 operates as an end-to-end system that receives a multi-channel EEG signal as an input and classifies the signal into one of four different categories indicating one of four icons being viewed by the driver 102.

The model 400 includes a residual neural network (ResNet) architecture and a squeeze and excitation (SE) block. The ResNet architecture has shown a remarkable ability to extract features from input data. In the model 400 of FIG. 4, the ResNet architecture has been combined with an SE block to further increase the feature extraction ability of the model.

In the example of FIG. 4, the SE block is responsible for improving the channel interdependencies and emphasizing the critical features. The SE block makes the model treat each feature map differently based on their importance by assigning them a weight. The SE block is able to dramatically improve the model performance in different applications.

In the example of FIG. 4, the model 400 includes a convolutional block 402, a first SE-Res block 404, a second SE-Res Block 406, and a classifier block 408. The convolutional block 402 includes a 2-dimensional convolutional layer 410, a batch normalization layer 412, and a rectified linear unit (ReLu) activation layer 414. The first SE-Res block 404 includes a 2-dimensional convolutional layer 416, a batch normalization layer 418, a ReLu activation layer 420, and an SE block 422. The second SE-Res block 406 includes a 2-dimensional convolutional layer 424, a batch normalization layer 426, a ReLu activation layer 428, and an SE block 430. The classifier block 408 includes a dropout layer 432, a fully connected layer with 4 units, and a softmax classifier 436. As shown in FIG. 4, the input to the first SE-res block 404 is summed to the output of the first SE-res block 404. Similarly, the input to the second SE-res block 406 is summed to the output of the second SE-res block 406.

Figure 5:
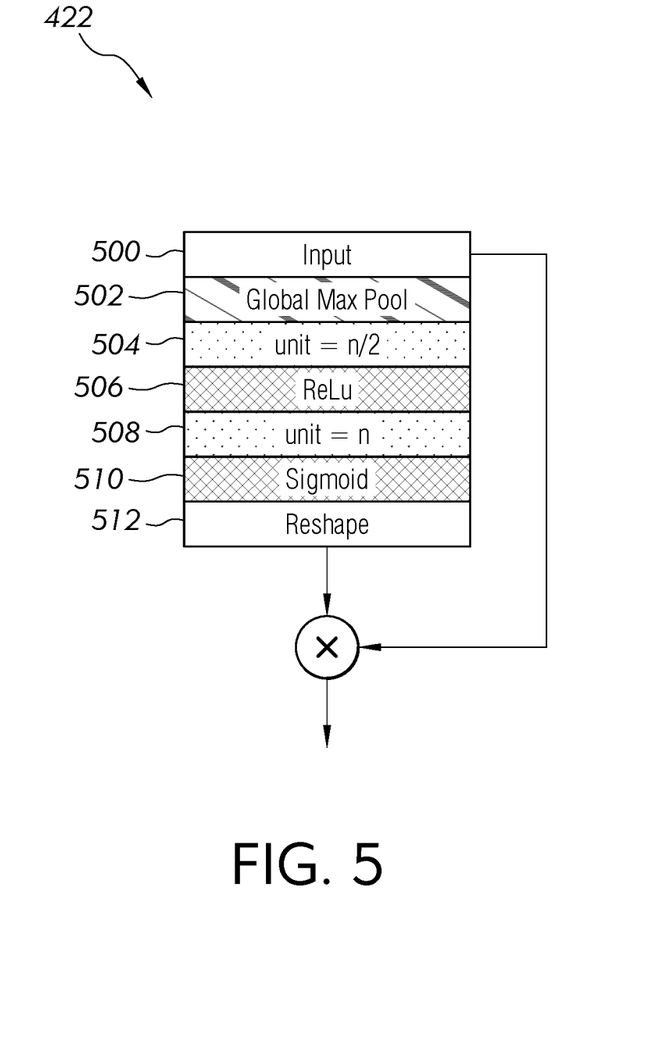
FIG. 5 depicts a schematic diagram of a an SE block of the machine learning model of FIG. 4, according to one or more embodiments shown and described herein.

The architecture of the SE block 422 of the first SE-Res block 404 is shown in FIG. 5. The SE block 430 of the second SE-Res block 406 is constructed similarly. The SE block 422 includes an input layer 500, a global max pooling layer 502, a first fully connected layer 504, a ReLu activation layer 506, a second fully connected layer 508, a Sigmoid activation layer 510, and a Reshape layer 512. The first fully connected layer 504 has a number of units equal to one half the number of inputs, and the second fully connected layer 508 has a number of units equal to the number of inputs. The fully connected layers 504 and 508 are responsible for giving a score to each feature map based on their importance in the final label. The scores are then applied to the input features by multiplication.

Referring back to FIG. 4, the dropout layer 432 helps to prevent overfitting to the particular training data used to train the model 400. In the illustrated example, a dropout value of 0.25 is used. However, in other examples, other dropout values may be used. In the example of FIG. 4, the input to the model 400 is a tensor of shape (C, F, 1) where C is the input channel, and F is the output of the FFT algorithm. The output of the model 400 is a vector of size 4 showing the class that the input data belongs to, which indicates which icon the driver 102 was viewing when the data was collected.

In the illustrated example, the model 400 is implemented in the Keras framework. However, in other examples, other frameworks may be used. In the illustrated example, a learning rate of 0.001 and a batch size of 32 were used. However, in other examples, other learning rates and/or batch sizes may be used.

Figure 6:
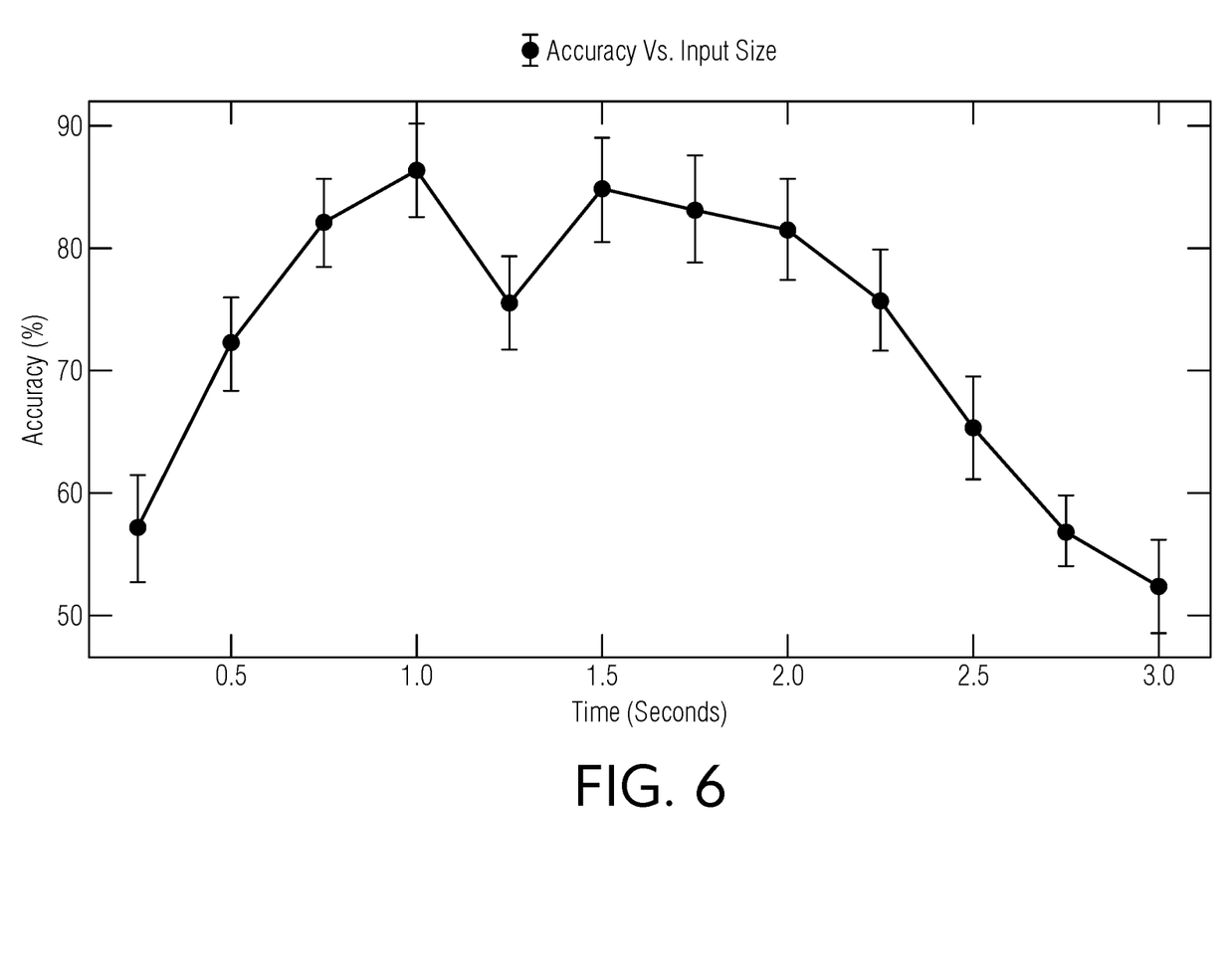
FIG. 6 depicts a plot of accuracy vs. input size for the machine learning model of FIG. 4, according to one or more embodiments shown and described herein.

In the illustrated example, accuracy of the model 400 was tested with different input sizes ranging from 0.25 seconds to 3 seconds with a step size of 0.25 seconds as shown in FIG. 6. As can be seen in FIG. 6, the highest accuracy is achieved with an input size of 1 second. Accordingly, in the illustrated example, an input size of 1 second is used. However, in other examples, a different input size may be used.

Referring back to FIG. 3, the model training module 310 may include programming instructions to train the model 400 of FIG. 4, maintained by the vehicle system 200. In particular, the model training module 310 may include programming instructions to train the model 400 based on the training data and ground truth values received by the training data reception module 300 after the data is preprocessed by the data filter module 304, the data segmentation module 306, and the FFT module 308. In the illustrated example, the model training module 310 includes programming instructions to train the model 400 in an end-to-end manner with the Adam optimization algorithm and binary cross entropy as the loss function for a maximum of 50 epochs using the early stopping strategy. However, in other examples, the model training module 310 may include programming instructions to use a different optimization algorithm, a different loss function, and/or a different number of epochs. After the model training module 310 trains the model 400, the learned model parameters may be stored in the data storage component 210.

Figure 7:
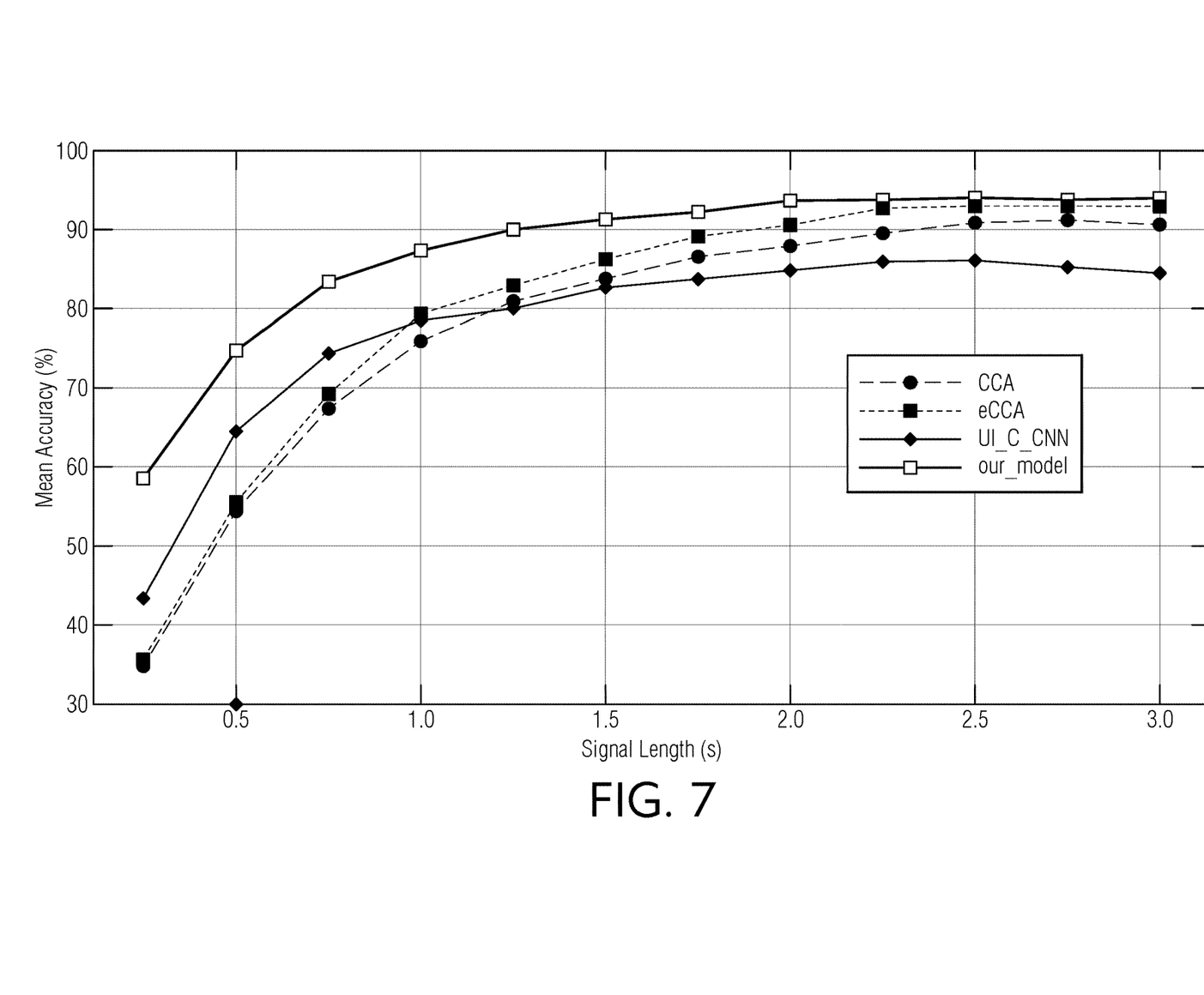
FIG. 7 depicts a plot of accuracy vs. signal length for the machine learning model of FIG. 4 and three other models, according to one or more embodiments shown and described herein.

To test the model 400 disclosed herein, accuracy of the model 400 was compared against several other models. In particular, the same training data was used for the disclosed model 400 and several known methods including canonical correlation (CCA), extended canonical correlation (eCCA), and user independent complex spectrum feature (UI-C-CNN). FIG. 7 shows the mean accuracy for each of these models for various signal lengths. As shown in FIG. 7, the disclosed model outperforms these known models for any signal length.

Referring back to FIG. 3, the icon detection module 312 includes programming instructions to detect an icon being looked at by the driver 102 on the HUD 108 in real-time using the model 400 after it has been trained by the model training module 310. In particular, while the driver 102 is viewing an icon on the HUD 108, the head-mounted device 104 may capture an EEG signal from the driver and transmit the signal to the brain wave data reception module 302. The received signal may be preprocessed by the data filter module 304, the data segmentation module 306, and the FFT module 308. The icon detection module 312 may then input the preprocessed signal into the trained model 400, and the model may output a prediction of which icon the driver 102 is viewing based on the input signal.

Referring still to FIG. 3, the vehicle system operation module 314 may include programming instructions to perform one or more vehicle operations based on the icon that the icon detection module 312 determines that the driver 102 is viewing. In one example, the vehicle system operation module 314 may cause the HUD 108 to display a different set of icons based on the icon being looked at by the driver 102 (e.g., a sub-menu of icons). In another example, the vehicle system operation module 314 may cause a function of the vehicle 100 to be stopped, started, or modified based on the icon being looked at by the driver 102.

In the example of FIG. 1, the icon in the HUD 108 being looked at by the driver 102 may cause the vehicle system operation module 314 to display a sub-menu of icons. For example, if the driver 102 views the icon 110, the vehicle system operation module 314 may display a sub-menu related to audio options; if the driver 102 views the icon 112, the vehicle system operation module 314 may display a sub-menu related to navigation options; if the driver 102 views the icon 114, the vehicle system operation module 314 may display a sub-menu related to settings; and if the driver 102 views the icon 116, the vehicle system operation module 314 may display a sub-menu related to temperature options.

A sub-menu may include icons to adjust different options or settings with respect to the vehicle. For example, after the driver 102 views the icon 116, the HUD 108 may display a sub-menu with different icons related to temperature settings. In particular, one of the icons of the sub-menu may relate to air conditioning, such that when the driver 102 views this icon, the vehicle system operation module 314 causes the air conditioning of the vehicle 100 to be started.

Referring back to FIG. 3, the icon color adjustment module 316 may include programming instructions to adjust one or more colors of icons displayed by the HUD 108, as disclosed herein. Research has shown that some people are better able to recognize certain colors. As such, the icon color adjustment module 316 may adjust the colors of icons displayed by the HUD 108 to be better recognized by the driver 102.

In one example, when the HUD 108 displays a sub-menu of icons, one of the icons may be used to return to the previous menu. This may allow the driver 102 to return to a previous menu and select a different sub-menu if the driver 102 inadvertently selected the wrong menu. If the driver 102 is utilizing this function often, it may indicate that the driver 102 is having difficulty recognizing the colors of the icons being displayed by the HUD 108, which is causing the driver 102 to select the wrong icons.

Accordingly, in embodiments, the icon color adjustment module 316 may include programming instructions to monitor how many times the driver 102 views and selects an icon to return to a previous menu. If the icon color adjustment module 316 determines that the driver 102 has utilized one of these icons more than a predetermined threshold number of times during a certain predetermined period of time, the icon color adjustment module 316 may adjust the color of one or more of the icons being displayed by the HUD 108 in order to assist the driver 102 to better recognize the icons and reduce the frequency of the driver 102 selecting the wrong icon. In some examples, when this determination is made, the icon color adjustment module 316 may adjust all of the colors of the icons being displayed by the HUD 108. In other examples, the icon color adjustment module 316 may identify the color of the icon that the driver 102 is most often incorrectly selecting and may adjust the color only of that icon.

Figure 8:
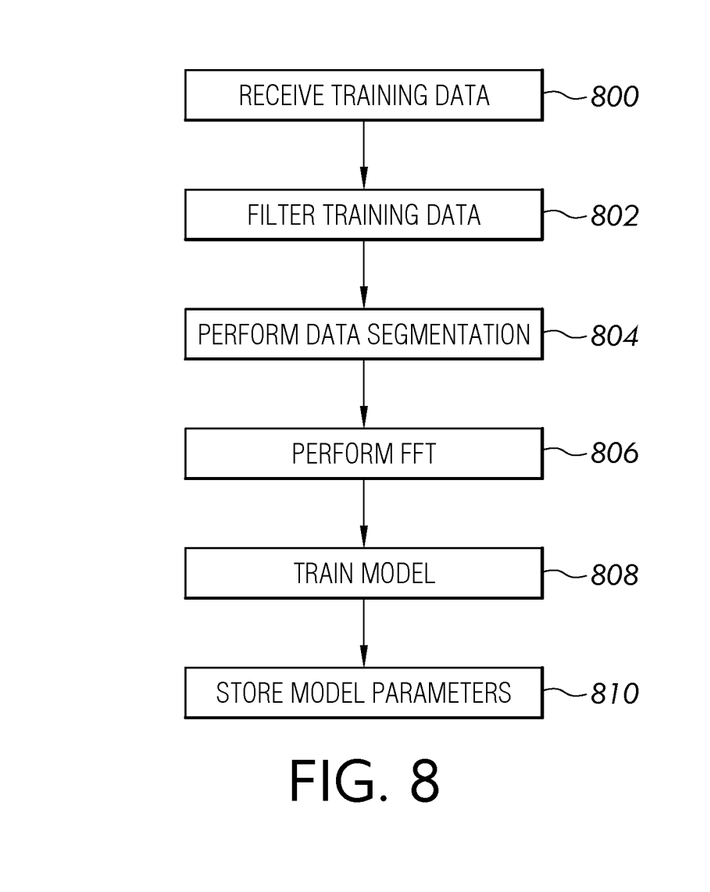
FIG. 8 depicts a flowchart for a method of operating the vehicle system of FIG. 2 to train the model of FIG. 4, according to one or more embodiments shown and described herein.

FIG. 8 depicts a flowchart of an example method of operating the vehicle system 200 to train the model 400. At step 800, the training data reception module 300 receives training data. As discussed above, the training data may include EEG data collected from a plurality of drivers wearing the head-mounted device 104 while viewing specific icons on the HUD 108. The training data may include ground truth values indicating which icon each driver was viewing during each time step.

At step 802, the data filter module 304 filters the training data received by the training data reception module 300. In the illustrated example, the data filter module 304 applies a Butterworth band pass filter between 3-40 Hz. However, in other examples, the data filter module 304 may apply other types of filters with other frequencies ranges.

At step 804, the data segmentation module 306 performs data segmentation of the training data received by the training data reception module 300. In the illustrated example, the data segmentation module 306 segments the training data into intervals of 0.25 seconds. However, in other examples, the data segmentation module 306 may segment the training data into intervals of other lengths.

At step 806, the FFT module 308 performs a FFT on the training data received by the training data reception module 300. In the illustrated example, the FFT module 308 uses a start and end frequency of 3 Hz and 35 Hz. However, in other examples, different start and/or end frequencies may be used.

At step 808, the model training module 310 trains the model 400 based on the training data received by the training data reception module 300, using the techniques described above. In the illustrated example, the model training module 310 trains the model 400 using the Adam optimization algorithm with binary cross entropy as the loss function, using a learning rate of 0.001 and a batch size of 32. However, in other examples, the model training module 310 may use other optimization algorithms, loss functions, learning rates, and batch sizes. After the model training module 310 trains the model 400, at step 810, the model training module 310 stores the learned parameters in the data storage component 210.

Figure 9:
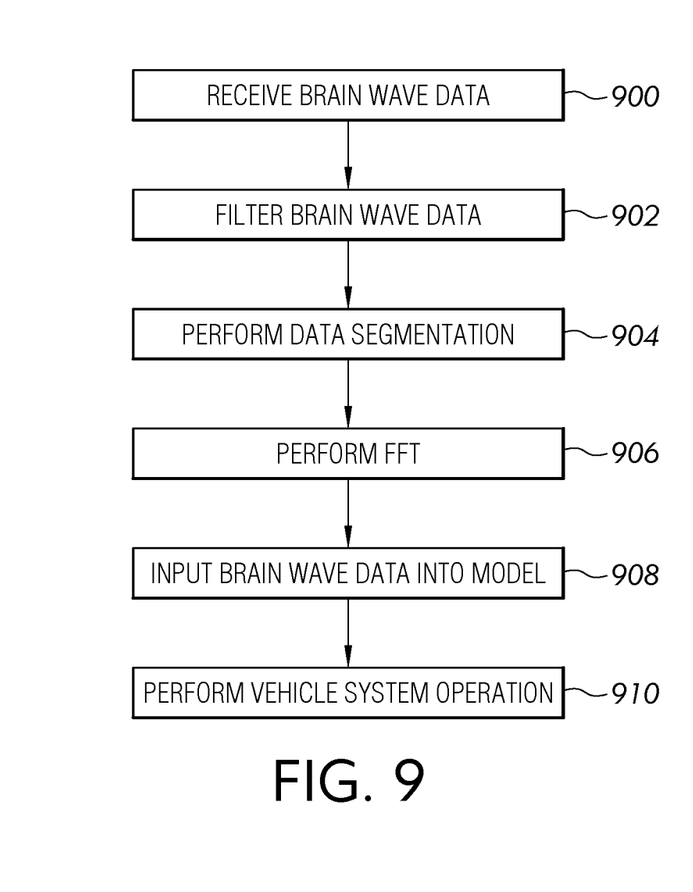
FIG. 9 depicts a flowchart for a method of providing the vehicle system of FIG. 2 to utilize the trained model of FIG. 4, according to one or more embodiments shown and described herein.

FIG. 9 depicts a flowchart of an example method of operating the vehicle system 200 after the model 400 has been trained. At step 900, the brain wave data reception module 302 receives brain wave data (e.g., EEG data) from the head-mounted device 104 worn by the driver 102 while the driver is viewing one of the icons displayed on the HUD 108. At step 902, the data filter module 304 filters the brain wave data received by the brain wave data reception module 302, as discussed above. At step 904, the data segmentation module 306 performs data segmentation of the brain wave data received by the brain wave data reception module 302, as discussed above. At step 906, the FFT module 308 performs a FFT on the brain wave data received by the brain wave data reception module 302, as discussed above.

At step 908, the icon detection module 312 inputs the inputs the preprocessed brain wave data into the trained model 400. The model 400 then outputs a prediction as to which icon the driver 102 is viewing. Then, at step 910, the vehicle system operation module 314 performs an operation of the vehicle system 200 based on the output of the model 400.

It should now be understood that embodiments described herein are directed to closed-loop real time SSVEP-based heads-up display to control in vehicle features using deep learning. As disclosed herein, a model maintained by a vehicle system may be trained to predict which icon of a HUD a driver is viewing based on EEG data. During real-time operation, EEG data may be received from a vehicle driver wearing a head-mounted device and input into the trained model. The trained model may predict which icon on the vehicle's HUD the driver is viewing. The vehicle system may then perform one or more vehicle operations based on the output of the model. The machine learning architecture and training methods of the embodiments disclosed herein may predict which icon the driver is viewing more quickly and accurately than known methods, thereby allowing for real-time operation while a vehicle is being driven.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A vehicle system, comprising a controller programmed to:
   display a plurality of icons on a heads-up-display (HUD) of a vehicle;
   receive electroencephalography (EEG) data from a driver of the vehicle;
   perform a Fast Fourier Transform (FFT) of the EEG data to obtain an EEG spectrum;
   input the EEG spectrum into a trained machine learning model that outputs a prediction of an icon that the driver is looking at based on the EEG spectrum;
   determine which of the plurality of icons the driver is viewing based on the output of the trained machine learning model; and
   perform one or more vehicle operations based on the output of the trained machine learning model.

2. The vehicle system of claim 1, wherein each of the plurality of icons has a different color.

3. The vehicle system of claim 1, wherein each of the plurality of icons has a different shape.

4. The vehicle system of claim 1, wherein the controller is further programmed to:
   apply a band pass filter to the EEG data to obtain filtered EEG data; and
   perform the FFT of the filtered EEG data.

5. The vehicle system of claim 1, wherein the controller is further programmed to:
   perform a data segmentation of the EEG data to obtain segmented EEG data; and
   perform the FFT of the segmented EEG data.

6. The vehicle system of claim 1, wherein the controller is further programmed to:
   receive training data comprising EEG data collected from a plurality of individual subjects while each subject is viewing specific icons; and
   train a machine learning model to predict which icon the individual subjects are viewing based on the training data to achieve the trained machine learning model.

7. The vehicle system of claim 1, wherein the trained machine learning model comprises a convolutional neural network.

8. The vehicle system of claim 7, wherein the convolutional neural network comprises a residual neural network architecture.

9. The vehicle system of claim 1, wherein the trained machine learning model comprises one or more squeeze and excite (SE) blocks.

10. The vehicle system of claim 9, wherein at least one of the SE blocks comprises a global max pooling layer, a first fully connected layer having a rectified linear unit activation function, and a second fully connected layer having a sigmoid activation function.

11. The vehicle system of claim 1, wherein the trained machine learning model comprises two SE-Res blocks, wherein each SE-Res block comprises:
   a two-dimensional convolutional layer;
   a batch normalization layer;

an activation layer; and an SE block.

12. The vehicle system of claim 11, wherein an input to each SE-Res block is summed with an output of the SE-Res block.

13. The vehicle system of claim 11, wherein the trained machine learning model further comprises:

a dropout layer; and a Softmax classification layer.

14. A method, comprising:

displaying a plurality of icons on a heads-up-display (HUD) of a vehicle;

receiving electroencephalography (EEG) data from a driver of the vehicle;

performing a Fast Fourier Transform (FFT) of the EEG data to obtain an EEG spectrum;

inputting the EEG spectrum into a trained machine learning model that outputs a prediction of an icon that the driver is looking at based on the EEG spectrum;

determining which of the plurality of icons the driver is viewing based on the output of the trained machine learning model; and performing one or more vehicle operations based on the output of the trained machine learning model.

15. The method of claim 14, further comprising:

apply a band pass filter to the EEG data to obtain filtered EEG data;

performing a data segmentation of the filtered EEG data to obtain segmented EEG data; and performing the FFT of the segmented EEG data.

16. The method of claim 14, wherein the trained machine learning model comprises a convolutional neural network comprising:

two SE-Res blocks, wherein each SE-Res block comprises:

a two-dimensional convolutional layer;

a batch normalization layer;

an activation layer; and an SE block.

17. The method of claim 16, wherein the SE block comprises a global max pooling layer, a first fully connected layer having a rectified linear unit activation function, and a second fully connected layer having a sigmoid activation function.

18. The method of claim 16, wherein the trained machine learning model further comprises:

a dropout layer; and a Softmax classification layer.

19. A method, comprising:

receiving training data comprising EEG data collected from a plurality of individual subjects while each subject is viewing specific icons;

performing an FFT of the training data to obtain EEG spectrum data; and training a machine learning model to predict which icon the individual subjects are viewing based on the EEG spectrum data.

20. The method of claim 19, wherein the machine learning model comprises:

two SE-Res blocks, wherein each SE-Res block comprises:

a two-dimensional convolutional layer;

a batch normalization layer;

an activation layer;

an SE block; and wherein the SE block comprises a global max pooling layer, a first fully connected layer having a rectified linear unit activation function, and a second fully connected layer having a sigmoid activation function.

* * * * *

UNITED STATES PATENT AND TRADEMARK OFFICE
CERTIFICATE OF CORRECTION

PATENT NO. : 12,358,370 B2
APPLICATION NO. : 18/067473
DATED : July 15, 2025
INVENTOR(S) : Hossein Hamidi Shishavan et al.

It is certified that error appears in the above-identified patent and that said Letters Patent is hereby corrected as shown below:

In the Specification

In Column 2, Line 5, after "diagram of", delete "a".

In Column 6, Line 13, delete "has" and insert --have--, therefor.

In Column 7, Line 11, delete "dated" and insert --data--, therefor.

In Column 8, Line 29, before "block", delete "SE-res" and insert --SE-Res--, therefor.

In Column 8, Line 29, after "first", delete "SE-res" and insert --SE-Res--, therefor.

In Column 8, Line 30, after "second", delete "SE-res" and insert --SE-Res--, therefor.

In Column 8, Line 31, after "second", delete "SE-res" and insert --SE-Res--, therefor.

In Column 10, Line 62, delete "frequencies" and insert --frequency--, therefor.

In the Claims

In Column 13, Line 26, Claim 15, delete "apply" and insert --applying--, therefor.

Signed and Sealed this
Twenty-third Day of September, 2025

John A. Squires
*Director of the United States Patent and Trademark Office*